(12) United States Patent
Chaffringeon et al.

(10) Patent No.: US 9,814,629 B2
(45) Date of Patent: Nov. 14, 2017

(54) APPLICATOR MEMBER AND FLEXIBLE RETENTION WEB DEVICE

(75) Inventors: Bernard Chaffringeon, Le Mont/Lausanne (CH); Richard Guetty, Miribel (FR)

(73) Assignee: V-Veil Shop Ltd., Nicosia (CY)

( * ) Notice: Subject to any disclaimer, the term of this patent is extended or adjusted under 35 U.S.C. 154(b) by 778 days.

(21) Appl. No.: 14/001,102

(22) PCT Filed: Feb. 21, 2012

(86) PCT No.: PCT/IB2012/000557
§ 371 (c)(1),
(2), (4) Date: Aug. 22, 2013

(87) PCT Pub. No.: WO2012/114200
PCT Pub. Date: Aug. 30, 2012

(65) Prior Publication Data
US 2013/0338567 A1    Dec. 19, 2013

Related U.S. Application Data

(60) Provisional application No. 61/445,851, filed on Feb. 23, 2011, provisional application No. 61/557,055, filed on Nov. 8, 2011.

(51) Int. Cl.
*A61F 13/26*    (2006.01)
*A61F 13/20*    (2006.01)
(Continued)

(52) U.S. Cl.
CPC .......... *A61F 13/26* (2013.01); *A61F 13/2062* (2013.01); *A61F 13/2065* (2013.01);
(Continued)

(58) Field of Classification Search
CPC .......... A61F 13/26; A61F 13/20; A61F 13/28; A61F 13/34
See application file for complete search history.

(56) References Cited

U.S. PATENT DOCUMENTS 1,884,089 A    10/1932 Millner
2,401,585 A    6/1946 Seidler
(Continued)

FOREIGN PATENT DOCUMENTS

EP    0104039 A1    3/1984
EP    0146320 A2    6/1985
(Continued)

OTHER PUBLICATIONS

International Search Report for International Application No. PCT/IB2012/000557, dated Sep. 13, 2012 (3 pages).

*Primary Examiner* — Ilya Treyger
(74) *Attorney, Agent, or Firm* — Osha Liang LLP

(57) ABSTRACT

A device and a method for manufacturing said device, the device comprising an applicator member and a flexible retention web (1) intended to be introduced into a vaginal cavity (17), said web being equipped with a means (7) for removal and being made from an a traumatic material whereof the dimensions are adapted so as to be able to retain and/or slow down bodily discharges of small quantity, characterized in that: —the applicator member comprises a body (8) that is at least partially hollow defining an internal storage volume (9), said body having a proximal end (10) on the one hand, and on the other hand, a distal end (11) intended to be inserted into the vaginal cavity of a user, said distal end having an open section emerging in the internal volume, —the web comprises a central zone (13) housed in the internal volume, and at least one peripheral zone (14) protruding from the body so as to cover at least the distal end of the body.

20 Claims, 8 Drawing Sheets

(51) Int. Cl.
*A61F 13/34* (2006.01)
*A61F 13/28* (2006.01)

(52) U.S. Cl.
CPC ...... *A61F 13/2077* (2013.01); *A61F 13/2085* (2013.01); *A61F 13/2097* (2013.01); *A61F 13/34* (2013.01); *A61F 13/206* (2013.01); *A61F 13/2057* (2013.01); *A61F 13/28* (2013.01)

(56) References Cited

U.S. PATENT DOCUMENTS

| | | | | |
|---|---|---|---|---|
| 3,431,909 A | * | 3/1969 | Krusko | A61F 13/2065 |
| | | | | 604/15 |
| 4,212,301 A | | 7/1980 | Johnson | |
| 5,817,077 A | * | 10/1998 | Foley | A61F 13/2051 |
| | | | | 604/363 |
| 6,177,608 B1 | | 1/2001 | Weinstrauch | |
| 6,899,700 B2 | * | 5/2005 | Gehling | A61F 13/2051 |
| | | | | 424/400 |

FOREIGN PATENT DOCUMENTS

| | | |
|---|---|---|
| EP | 2276441 | 1/2011 |
| WO | 03/051257 A1 | 6/2003 |
| WO | 20091112527 A1 | 9/2009 |

\* cited by examiner

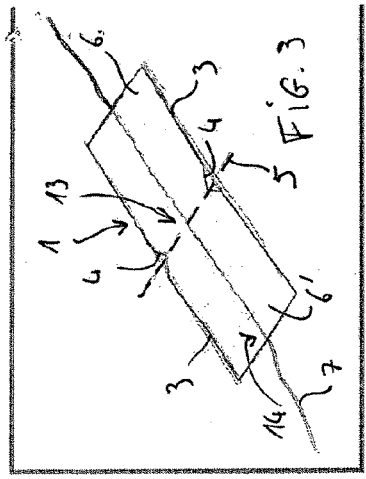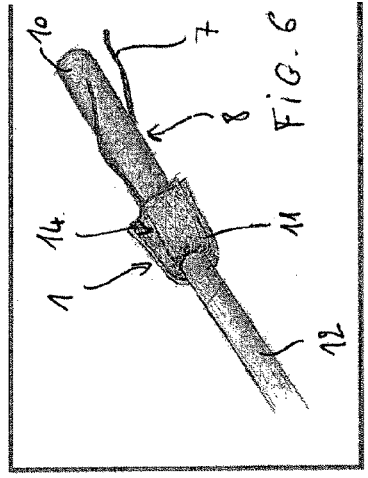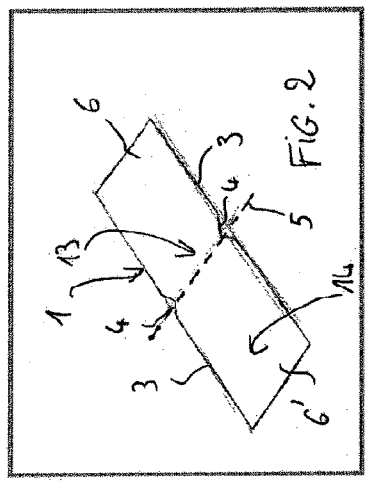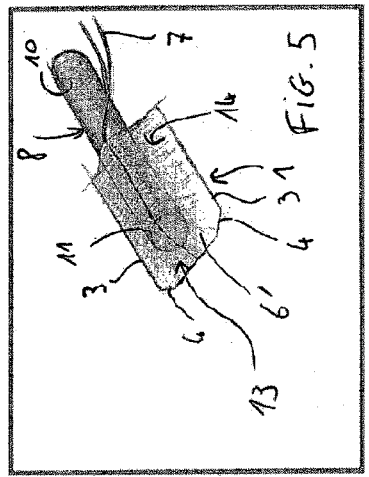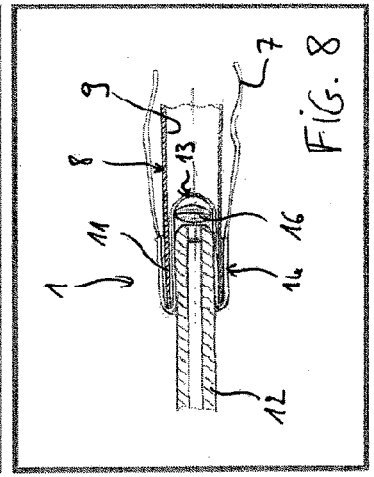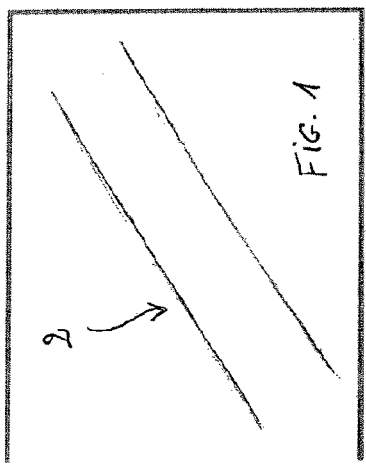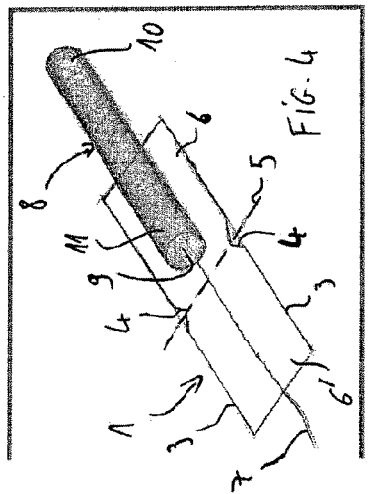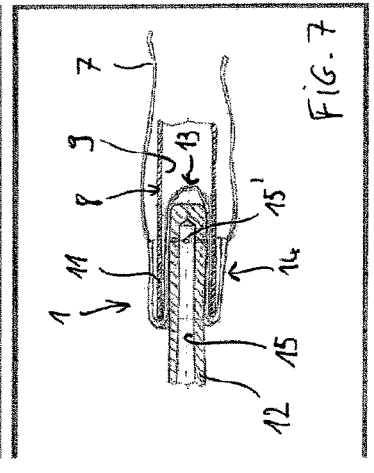

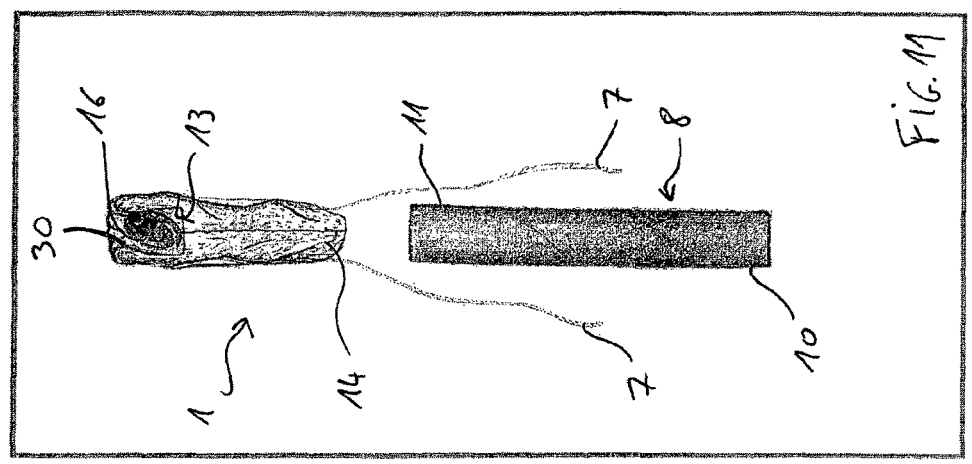
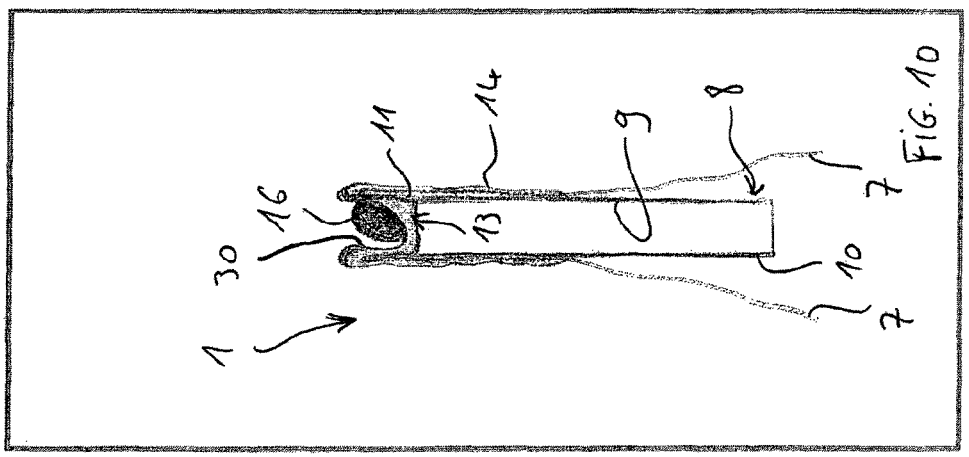
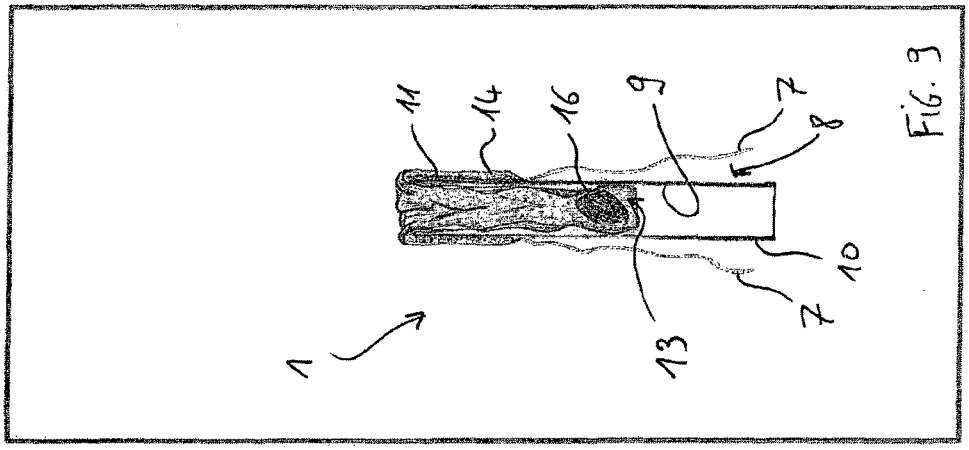

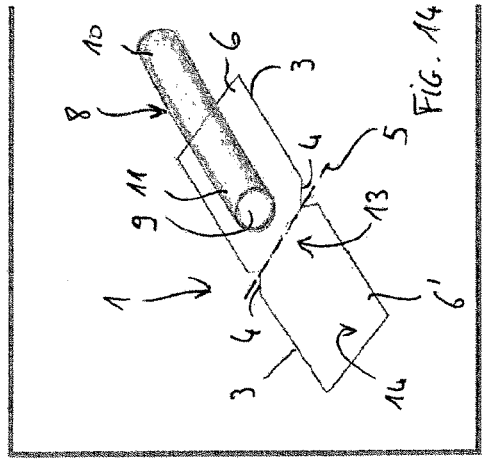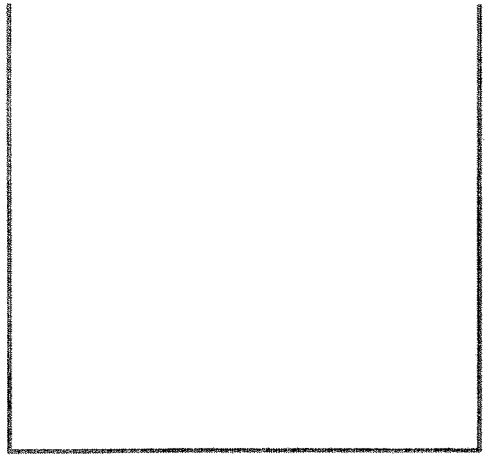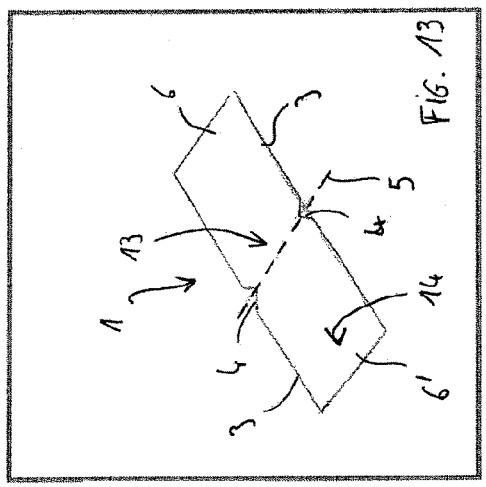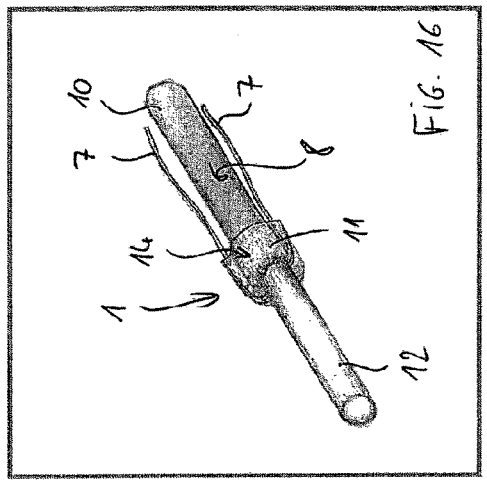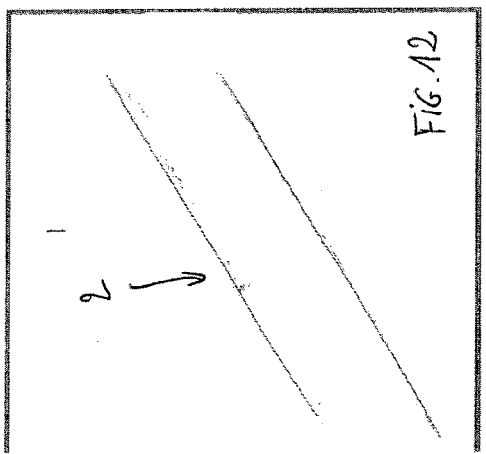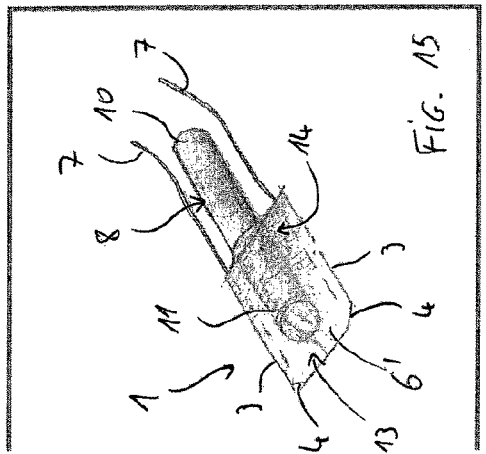

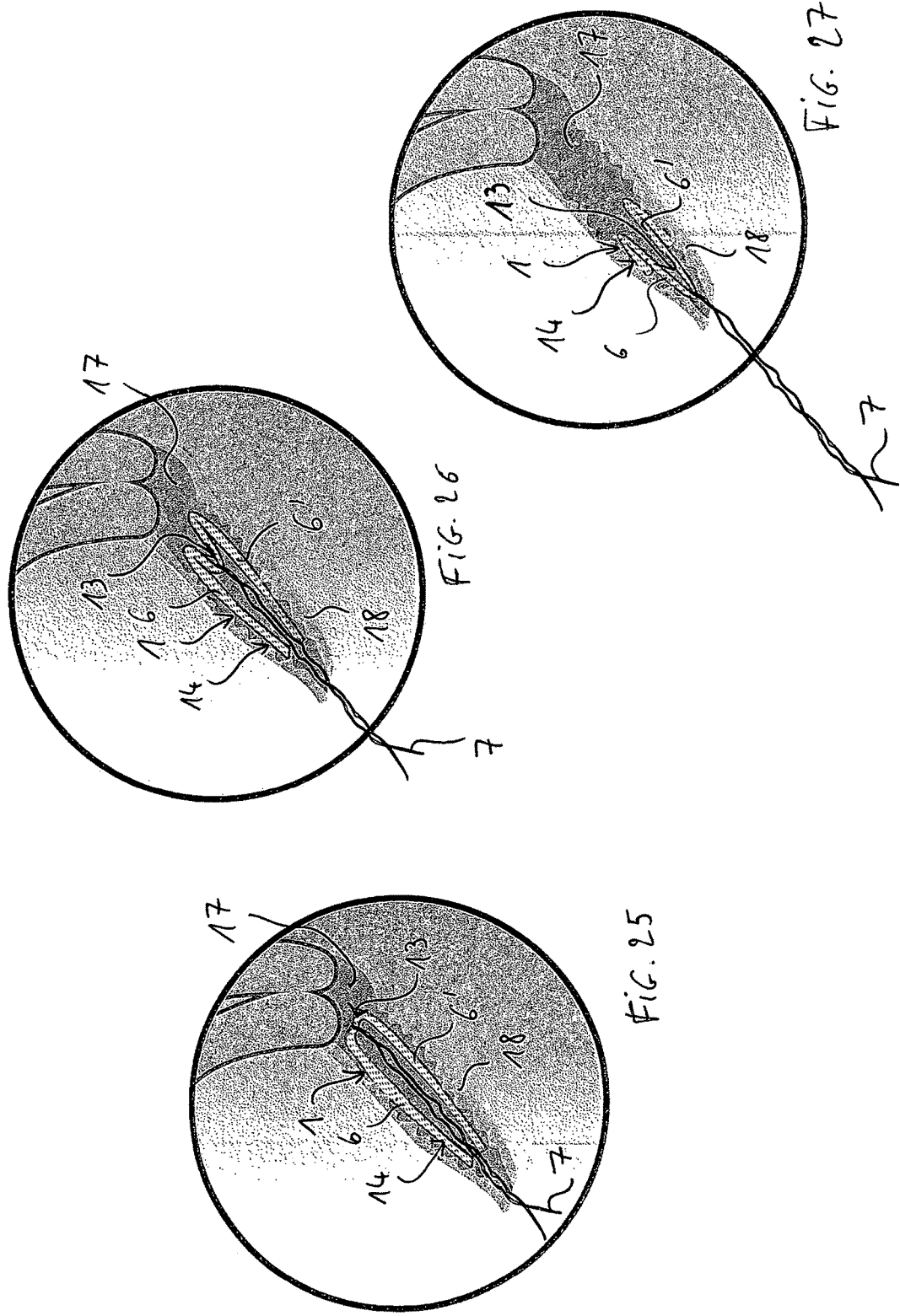

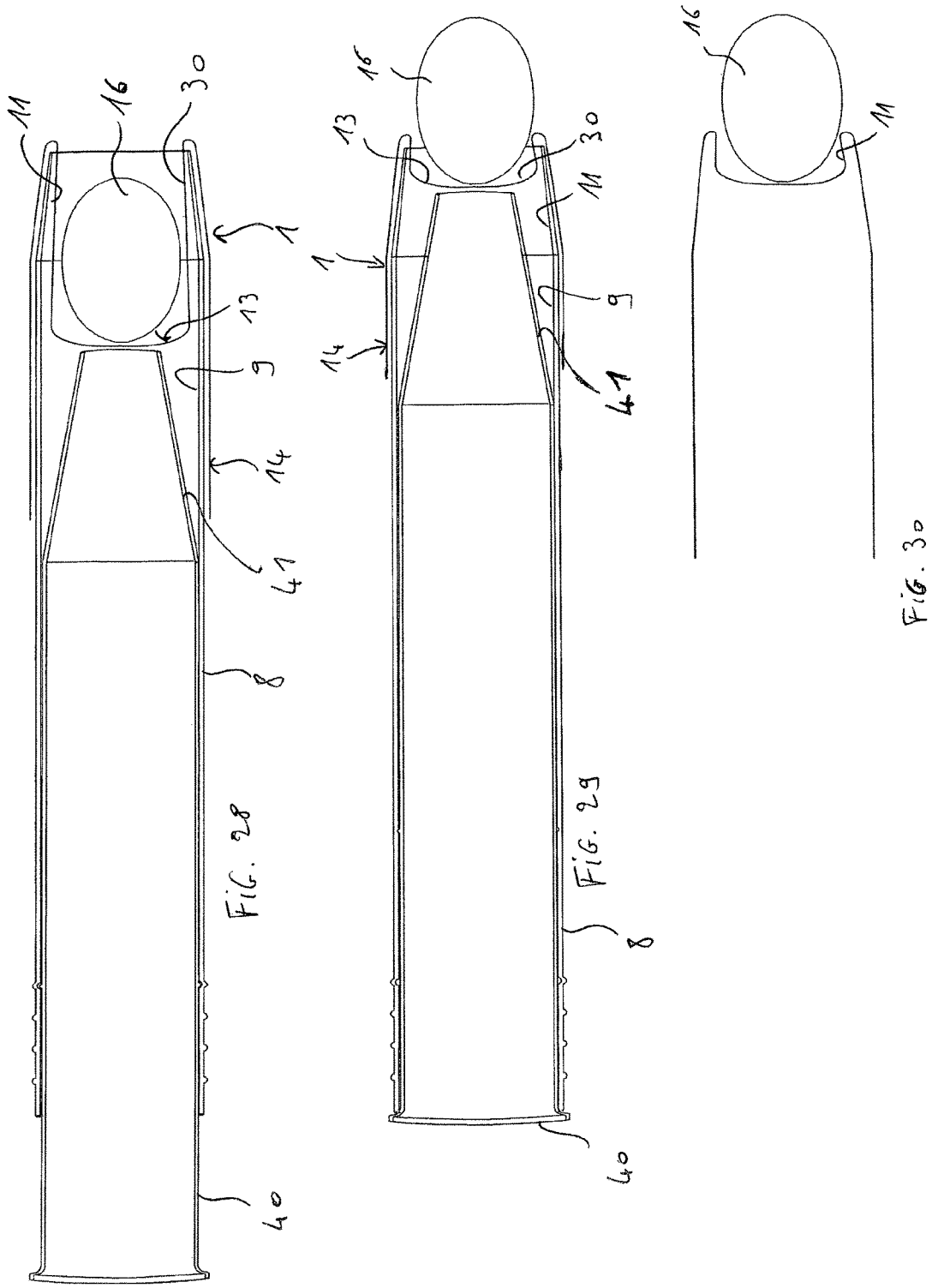

APPLICATOR MEMBER AND FLEXIBLE RETENTION WEB DEVICE

The present invention relates to the field of devices for absorbing discharges of bodily fluids, for example menstrual flows and cervical mucus, and/or discharges related to the intromission of at least one therapeutic or non-therapeutic agent in a vaginal cavity.

Many hygiene articles exist, especially for absorbing menstrual flows, for example period tampons and/or bands that are folded and/or rolled up using techniques well known by those skilled in the art to form bodies that are able to dilate once they have been placed, with or without applicators, in the vaginas of the users.

This type of device is commonly used regardless of the volume of secretions to be absorbed and is generally designed in such a way as to be able to retain a moderate or even substantial flow (from 6 to 18 g), so that it is suitable for the greatest possible number of people.

However, users who produce bodily discharges of small quantity, i.e. less than 6 g, are faced with the fact that the inserted tampon is not appropriate for the volume of their secretions. The contact of the rough and more or less dilated tampon against the dry wall of the vagina results in pain, local irritation, and thus causes trauma to the person using it. This sensation of discomfort is all the more pronounced when the tampon is being removed. Moreover, independently of the question of user comfort, it should be noted that the use of such large amounts of material for absorbing small volumes of discharge runs counter to the generally accepted environmental policy of reducing the amounts of waste material.

To improve tampons of this kind, document U.S. Pat. No. 6,177,608 discloses a tampon comprising an absorbent core and a permeable cover which is disposed around the core and which is provided with strips which form funnels that can be spread out from the core in such a way as to obstruct a free space formed between the outer surface of the tampon and the wall of the vagina. This makes it possible in particular for the fluid received by the funnels to converge toward the absorbent core.

Moreover, document WO 03/051257 provides a flexible tampon comprising a substantially flat absorptive central core arranged between two protective permeable layers. Such a tampon is intended to be used in place of a traditional tampon and is distinguished by the fact that it can be folded around the user's finger so as to be introduced gently into the vaginal cavity.

This principle for the design of a tampon has nevertheless been anticipated for some time by document U.S. Pat. No. 1,884,089, which proposes the production of a sanitary article in the form of a disc made of a highly compressed absorbent material so as to absorb standard volumes or even copious volumes of bodily discharges. This disc is folded around the finger and introduced into the vaginal cavity with the finger, and a string forming a means of removal is securely attached to the center of the disc. However, the zone of attachment of the string to the disc constitutes a hard spot that may damage the wall of the vagina during the use or removal of the disc. The same applies to document WO 03/051257, where the attachment of the string to the tampon also creates a hard spot.

Patent application EP 2 276 441 discloses a retention web making it possible to resolve all of the abovementioned drawbacks, this web more particularly being intended for users who produce small volumes of bodily secretions.

The present invention in particular aims to propose one alternative embodiment and use of such a web. Out of a concern for clarity and concision, most of the compatible technical features between the web according to EP 2 276 441 and the web according to the present invention will not be mentioned explicitly in this patent application, but it must be understood that they are incorporated overall by reference.

The present invention consists of a device comprising an applicator member and a flexible retention web intended to be introduced into a vaginal cavity, said web being equipped with a means for removal and being made from an atraumatic material whereof the dimensions are adapted so as to be able to retain and/or slow down bodily discharges of small quantity, characterized in that:

the applicator member comprises a body that is at least partially hollow defining an internal storage volume, said body having a proximal end on the one hand, and on the other hand, a distal end intended to be inserted into the vaginal cavity of a user, said distal end having an open section emerging in the internal volume, the web comprises a central zone housed in the internal volume, and at least one peripheral zone protruding from the body so as to cover at least the distal end of the body.

Thus, a device according to the invention may, if necessary, be a catemenial and/or sanitary device intended to replace a traditional tampon, and/or a medical device capable of delivering at least one therapeutic or non-therapeutic agent in the vaginal cavity of a user.

Within the meaning of the present invention, it should be understood that the expression "small quantity" means that the web is solely intended to retain bodily discharges in volumes much lower than those normally collected by traditional tampons, especially during menstruation. To this end, the web is designed to have no excess thickness of unnecessary material.

Such a web is therefore particularly adapted to afford exceptional usage comfort to a user who produces small amounts of bodily discharge, for example as a result of regular use of a contraceptive, or whose menstrual flow is limited, particularly at the end of the cycle. The web may have more or less absorbent qualities, depending on the desired use. Certain discharges, for example cervical mucus, will tend more to be deposited on the surface of the web, and to be kept there due to their viscosity. It must be understood that the retention phenomenon of the discharges on the web may apply, even in the case where the web is made from a material with little or no absorbency, by forming an adapted relief on the surface of the Web so as to slow down the speed of propagation of the discharges toward the outlet of the vaginal cavity.

A device according to the invention will be particularly adapted in the following situations:

At the end of menstrual periods, when the flow is light (less than 6 g),

In case of low- or medium-intensity metrorrhagia, for example upon changing contraceptive pills or after placing an intrauterine contraceptive device, In women with physiological leukorrhea, After sexual relations to collect the sexual secretions.

Preferably, the applicator member is made in the form of a tubular body.

Also preferably, the distal end is made in the form of a substantially conical segment so as to have a reduced passage section relative to the diameter of the body, and the segment is designed so as to have a radial elasticity.

Advantageously, the web is made from a material chosen from amongst the group formed by a nonwoven textile, polyvinyl acetate, cotton, an organic material, a plant material, or a biodegradable material.

Also advantageously, the web is designed such that it can convey at least one therapeutic or non-therapeutic agent, for example having healing, lubricating, anticoagulant, or antioxidant properties. To that end, the therapeutic or non-therapeutic agent may for example be made in the form of:
- a substance impregnated in the web,
- a capsule, a suppository, a cream, or a dry vaginal suppository supported by the web.

Preferably, the web is made in a substantially rectangular, square, oval or circular shape.

When one wishes to deliver a pharmaceutical or non-pharmaceutical substance, the web will be designed so that it can maintain a maximum quantity of substance on the surface of the web, during as long a period of time as possible, with the aim of obtaining optical contact of the substance with the mucosa to be treated, and therefore a better exchange between them. In fact, given its small thickness and its particular texture, this web coated with the substance will hug the internal relief of the vaginal cavity as well as possible. Such a result cannot be obtained with an absorbent web that attracts and captures the substance in the thickness thereof, as such a web results in creating an unwanted adsorption phenomenon and has a smaller deformation capacity and therefore adaptation capacity to the internal relief of the vaginal cavity.

Also preferably, the web comprises at least two flaps folded onto each other.

Advantageously, each of the two flaps is extended by a removal means.

Alternatively, a removal means is attached to the central zone of the web, and the body of the applicator member is hollow. Preferably, the removal means is disposed along the transverse axis.

According to one alternative embodiment, the web incorporates at least one fluid barrier made using a hydrophobic material, of the Vaseline or beeswax type, for example.

The present invention also relates to a method for manufacturing a device according to the invention, characterized in that it comprises the following steps:
- cutting a web in a band,
- depositing and fastening, on the web, at least one string, for example of the chain stitch type, forming a removal means, the length of the string being chosen to be greater than the largest length of the web so that the string protrudes on either side of the web,
- depositing the applicator member along part of the web, so that, on the one hand, the proximal end protrudes from the web, and on the other hand, the distal end rests on the web,
- folding the web around a transverse axis, and folding the web on the applicator member,
- inserting the central zone of the web into the internal volume of the applicator member using an insertion member.

It must be understood that these steps are not necessarily carried out in this chronological order. As an example, the removal means may in some cases be incorporated after deposition of the applicator member.

According to a first alternative embodiment, a single string is deposited and secured substantially along the median longitudinal axis of the web.

According to a second alternative embodiment, a string is deposited and secured along each of the two longitudinal edges of the web.

Preferably, the applicator member is deposited so that its distal end is situated substantially at mid-length of the web.

Advantageously, a notch is cut into each of the two longitudinal edges of the web at the transverse axis. This makes it possible to limit the risks of injury or irritation due to the friction of the web at its transverse folding axis with the vaginal wall of the user.

According to another alternative embodiment, at least one therapeutic or non-therapeutic agent is injected on the central zone of the web through at least one conduit and an injection opening of the insertion member.

According to another alternative embodiment, before insertion of the central zone of the web into the internal volume, a therapeutic or non-therapeutic agent, of the capsule, suppository, cream, or dry vaginal suppository type, for example, is positioned between the central zone of the web and the insertion member.

Furthermore, the length of the web may be chosen so that, after complete insertion of the applicator into the vaginal cavity, part of the central zone of the web as well as the agent remain in the internal volume. A pouch containing the agent will thus be formed in the internal volume. After removal of the applicator member, this pouch will remain present in the vaginal cavity, and will allow the agent to remain fully in contact with the zone to be treated. Furthermore, this pouch will make it possible to collect at least part of the future discharges, in particular due to the decomposition of the agent.

More generally, it must also be understood that such a pouch may advantageously be formed, even when no therapeutic or non-therapeutic agent will be delivered. In fact, in such a scenario, this pouch will make it possible to collect at least part of the bodily discharges delivered by the user.

The present invention also relates to another method for manufacturing a device according to the invention, characterized in that it comprises the following steps:
- cutting a web in a band,
- depositing and fastening, in the central zone, at least one string forming a removal means,
- inserting the free ends of each string into the body of the applicator member,
- inserting the central zone of the web into the internal volume of the applicator member by pulling on the free ends of each string, and/or potentially by pushing using an insertion member.

It must be understood that these steps are not necessarily carried out in that chronological order.

As a result, the removal means thus secured on the web allow the user to pull on that removal means to safely and easily extract the web from the vaginal cavity.

Preferably, a notch is cut into each of the two longitudinal edges of the web at the transverse axis.

So as to still further optimize this manufacturing and assembly method, the removal means is positioned in the direction of the width of the web, and is preferably attached to the central zone along the transverse axis.

According to one alternative embodiment, at least one therapeutic or non-therapeutic agent is injected on the central zone of the web through at least one conduit and an injection opening of an insertion member.

According to still another alternative embodiment, after insertion of the central zone of the web into the internal volume, one arranges a therapeutic or non-therapeutic agent, of the capsule, suppository, cream, or dry vaginal suppository type, for example, on said central zone.

Also advantageously, the length of the web is chosen so that, after total insertion of the applicator member into the vaginal cavity, part of the central zone of the web as well as the agent remain in the internal volume.

The invention will be better understood using the detailed description provided below in light of the appended drawing, in which:

FIGS. 1 to 6 are diagrammatic perspective views illustrating the successive steps of manufacturing a device according to a first embodiment of the invention;

FIG. 7 is a partial longitudinal cross-sectional view of a device according to one embodiment of the invention;

FIG. 8 is a partial longitudinal cross-sectional view of a device according to another alternative embodiment of the invention;

Figure 22:
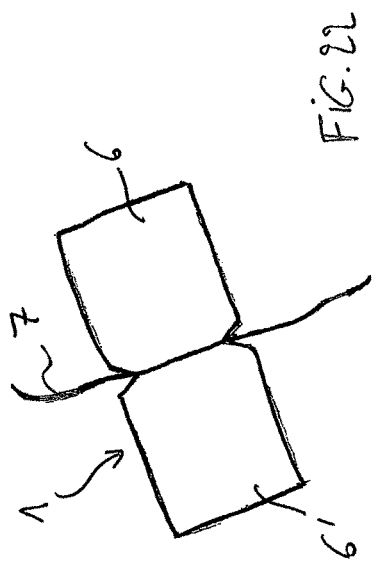
Figure 24:
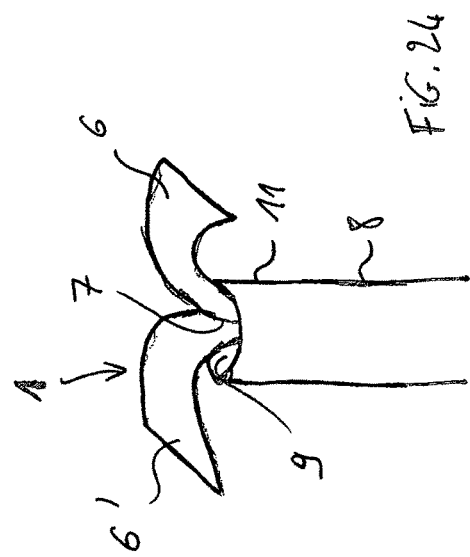
Figure 23:
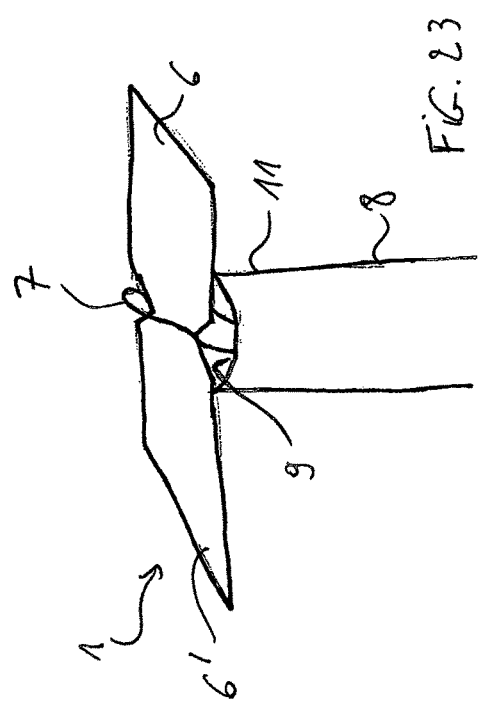
Figure 31:
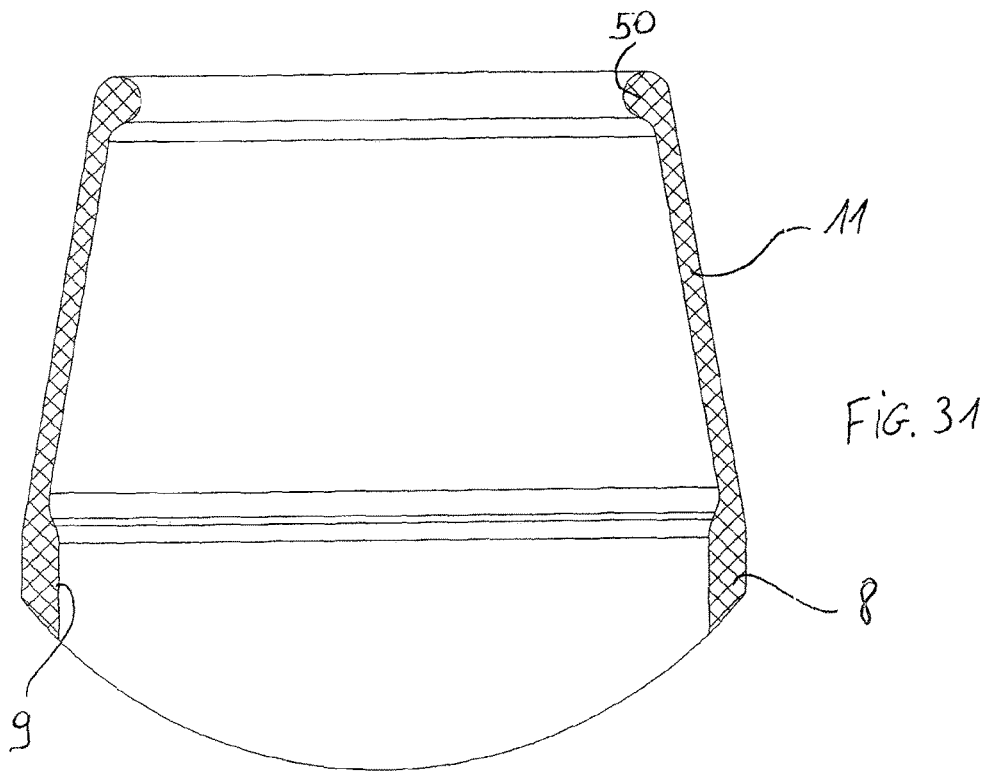
Figure 32:
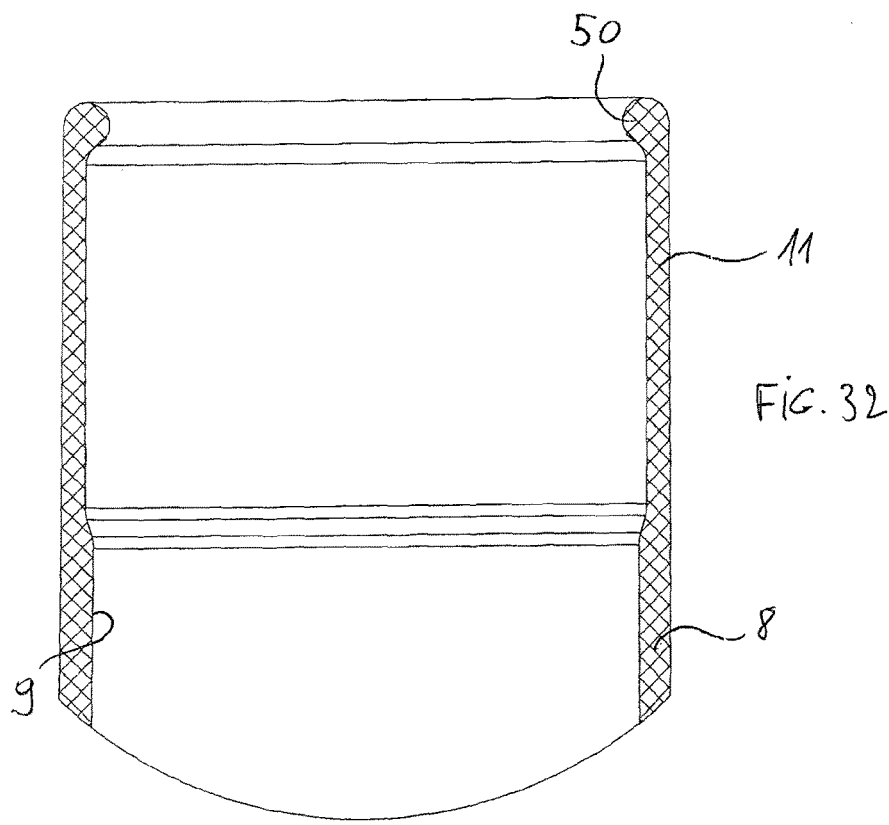

FIGS. 9, 10 on the one hand, and FIG. 11 on the other hand, are respectively longitudinal cross-sectional and perspective views illustrating the successive intromission steps of a device according to another alternative embodiment of the invention;

FIGS. 12 to 16 are diagrammatic perspective views illustrating the successive steps of manufacturing a device according to a second embodiment of the invention;

FIGS. 17 to 21 are diagrammatic side views illustrating the successive intromission steps of a device according to the invention in a vaginal cavity of a user;

FIGS. 22 to 24 are diagrammatic perspective views illustrating the successive steps of manufacturing a device according to a third embodiment of the invention;

FIGS. 25 to 27 are diagrammatic longitudinal cross-sectional views illustrating the successive steps during the removal of a device according to the invention from a vaginal cavity;

FIGS. 28 to 30 are diagrammatic longitudinal cross-sectional views illustrating the successive steps for releasing an agent, of the dry vaginal suppository type for example, equipping a specific applicator member;

FIG. 31 is a detailed view of the body of the applicator member shown in FIG. 28;

FIG. 32 is a detailed longitudinal cross-sectional view of a component body of another device according to the invention.

In the following detailed description of the figures defined above, identical elements or elements performing identical functions may keep the same references so as to simplify the understanding of the invention.

The method for manufacturing a device according to a first embodiment of the invention, as shown in FIGS. 1 to 6, comprises the following steps.

First, a web 1 with an adapted length, typically a length smaller than 20 cm, is cut into a band 2. The shape of that band 2 is preferably similar to that used to produce traditional tampons. There is therefore no need to develop a specific substitution technology to produce the web 1. The web 1 is therefore made in the form of a rectangular body having two large sides each making up a longitudinal edge 3.

In FIG. 2, a notch 4 is cut into each of the two longitudinal edges 3 of the web 1, at a median transverse axis 5 dividing said web 1 into two flaps 6, 6' with substantially equal dimensions.

In FIG. 3, a string 7 forming a chain stitch is deposited and secured along the median longitudinal axis of the web 1. This string 7 has a larger length than that of the web 1, so as to protrude on either side of the web 1. Thus, this string 7 forms the means for removing the web 1.

Of course, this step for depositing and securing the string 7 could alternatively be made before cutting out the notches 4.

In FIG. 4, an applicator member made in the form of a tubular body 8 delimiting a hollow internal volume 9 is deposited on the web 1. This body 8 comprises a side wall having a proximal end 10 and a distal end 11. The applicator member is disposed so that, on the one hand, its proximal end 10 protrudes from the web 1, and on the other hand, its distal end 11 rests on the flap 6 and is situated slightly withdrawn from the transverse axis 5.

Then, and as shown in FIG. 5, the flap 6' is folded around the transverse axis 5 and folded down on the applicator member.

Lastly, an insertion member, made in the form of an insertion shaft 12, is used to make the central zone 13 of the web 1 penetrate into the internal volume 9 of the body 8. Of course, to that end an insertion shaft 12 is used whereof the diameter is smaller than that of the body 8.

In so doing, the peripheral zone 14 surrounding the central zone 13 of the web 1 remains outside the body 8, and covers at least part of the external side wall of the body 8 at its distal end 11.

As shown in FIG. 7, the insertion shaft 12 can comprise at least one conduit 15 and an injection orifice 15' making it possible to inject a therapeutic or non-therapeutic agent, for example of the liquid, gel, particulate, micro-particulate, etc. type. Thus, during insertion of the central zone 13 into the internal volume 9 using the insertion shaft 12, it is in parallel possible to inject such an agent on at least part of said central zone 13.

Alternatively, and as shown in FIG. 8, the insertion shaft 12 can be used to slide a therapeutic or non-therapeutic agent 16, of the capsule, suppository, cream, or dry vaginal suppository type, for example, into the internal volume 9 so as to position it in contact with the central zone 13.

Alternatively, and as shown in FIGS. 9 to 11, the device differs from that covered by FIG. 8 inasmuch as the web 1 is longer. In so doing, during use, when the applicator member 8 abuts at the back of the vaginal cavity (not shown), part of the central zone 13 of the web 1 remains in the internal volume 9 and defines a pouch 30 therein in which the agent 16 remains housed. After removing the applicator member 8, and as shown diagrammatically in FIG. 11, this pouch makes it possible to keep the agent 16 in contact with the zone to be treated at the back of the vaginal cavity.

Furthermore, this pouch 30 makes it possible to collect part of the discharges that are produced, in particular due to the decomposition of the agent 16.

The method for manufacturing a device according to a second embodiment of the invention, as shown in FIGS. 12 to 16, differs from the first embodiment only as regards the step for integrating the removal means.

More specifically, and as illustrated in FIG. 15, after having folded the flap 6' down on the flap 6, a string 7, of the chain stitch type, is deposited and loosely bent along each of the two longitudinal edges 3 of the web 1.

In this embodiment, the strings 7 thus also form lateral connecting means of the flaps 6, 6', so that the distal end 11 of the body 8 cannot be laterally extracted from the web 1.

The method for manufacturing a device according to a third embodiment of the invention, as shown in FIGS. 22 to 24, differs from the previous two embodiments primarily as regards the step for incorporating the removal means.

More specifically, and as shown in FIG. 22, a string 7 is disposed on the web 1 at the transverse axis 5. It should be noted that this string 7 can be secured on the surface of the web 1, or, in the thickness of the web 1 if that thickness is sufficient. The attachment of the string 7 to the web 1 can be obtained by welding, ultrasound welding, sewing, weaving, knotting (lasso or choker type), adhesion, or any means allowing an effective connection and allowable with the expected usage of the device.

The web 1 is then positioned on the distal end 11, as shown in FIG. 23, while taking care to insert the string 7 into the hollow body 8 of the applicator member.

It then suffices to pull on the two ends of the string 7 to cause an optimal insertion of the central zone 13 of the web 1 into the body 8, as shown in FIG. 24. Alternatively, or additionally, an insertion member 12 may be used to insert said central zone 13 into the body 8.

FIGS. 17 to 21 show the successive intromission steps of a device according to the invention in a vaginal cavity 17 of a user.

Figure 17:
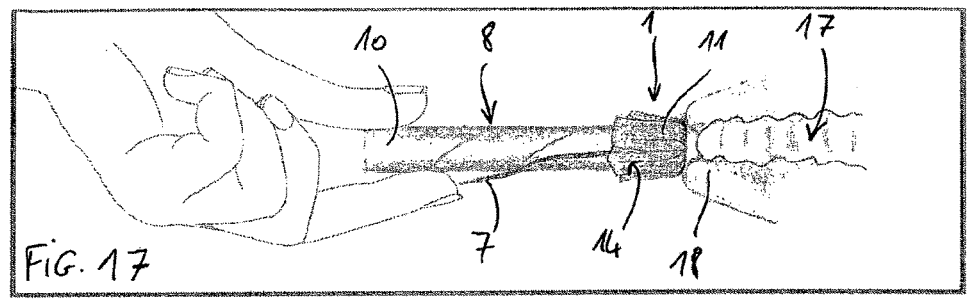

In FIG. 17, the user has grasped the device by the proximal end 10 of the body 8, and introduces the distal end 11 opposite the vaginal wall 18.

Figure 18:
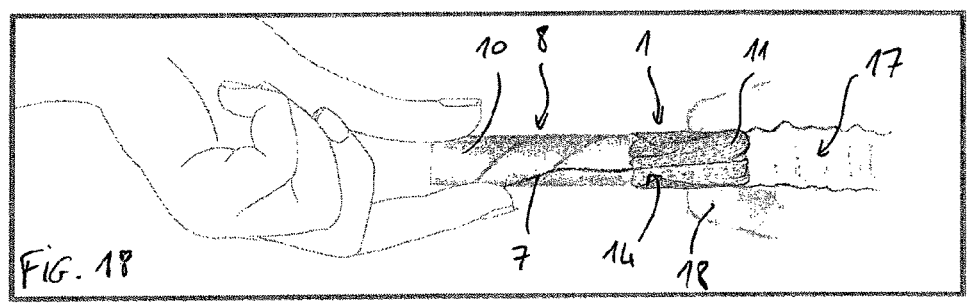
Figure 19:
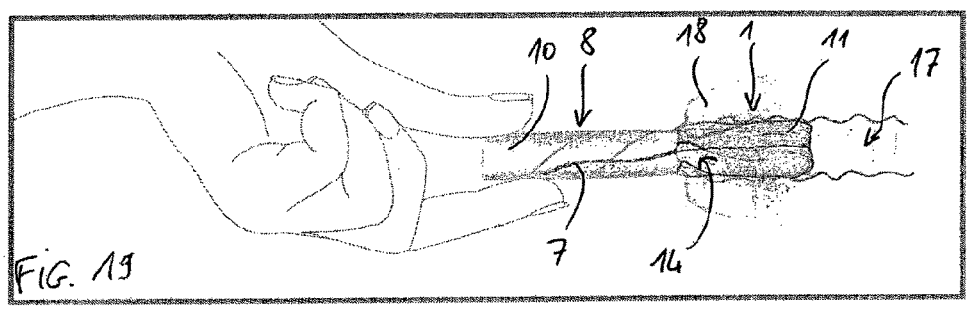

In FIG. 18, the distal end 11 has started to penetrate the vaginal cavity 17 after the vaginal wall 18 has moved away. In so doing, the vaginal wall 18 exerts an annular pressure on the peripheral zone 14 of the web 1 disposed around the distal end 11. This pressure being substantial enough to pinch the peripheral zone 14 on the distal end 11, the thrust exerted by the user on the applicator member, so as to force the latter to translate along the vaginal cavity 17, thereby causes the unrolling of the web 1 by extraction of the central zone 13 of the web 1 from the internal volume 9. During this unrolling of the web 1, it is very interesting to note that no friction is generated between the web 1 and the vaginal wall 18 since the web 1 does not translate. This therefore makes it possible to greatly decrease the risk of lesions or irritations of the vaginal wall 18.

Figure 20:
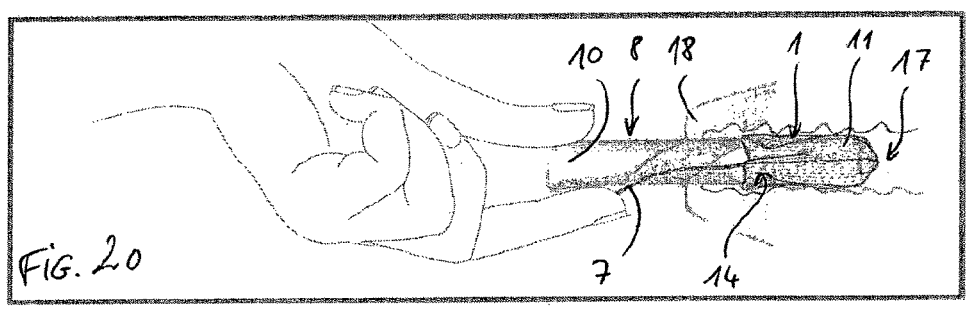

When the web 1 is completely unrolled, i.e. when the central zone 13 of the web 1 is therefore completely dislodged from the internal volume 9, the web 1 accompanies the translation of the applicator member until the web 1 is disposed suitably within the vaginal cavity 17 (FIG. 20). The friction surface between the web 1 and the vaginal wall 18 is therefore minimal during this step.

It should be noted that the method for manufacturing a device according to the third embodiment makes it possible to obtain specific crucial advantages.

First, the string 7 being housed in the body 8, as a result the string 7 no longer engages in friction with the vaginal wall 18 during the sliding of the applicator member. For the same reason, there is no risk of the string 7 remaining stuck between the applicator member and the user's fingers.

Figure 21:
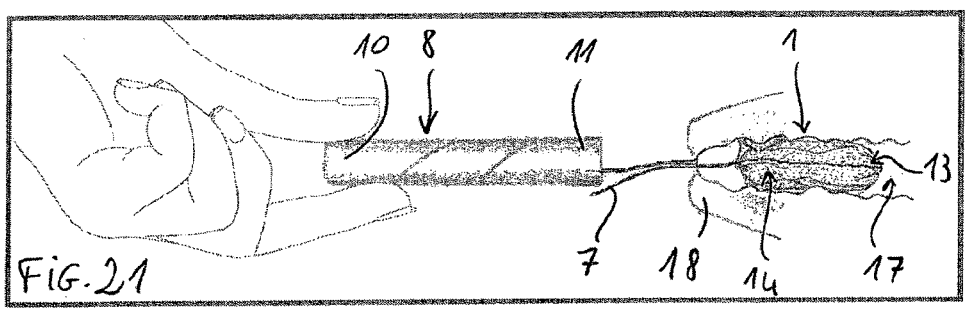

As shown in FIG. 21, the user then need only remove the applicator member through a reverse translation movement. The web 1 remains in place in the vaginal cavity 17.

The user then need only pull on the removal means 7 to remove the web 1 when necessary.

FIGS. 25 to 27 specify how the web 1, obtained according to the third embodiment of the invention, is removed from the vaginal cavity 17.

In FIG. 25, the web 1 is shown as introduced into the vaginal cavity 17. Unlike all of the known tampon systems, the attachment zone of the string 7 to the web 1 is then as deep as possible in the vaginal cavity 17.

During the removal, and as shown in FIG. 26, the central zone 13 of the web 1 gradually moves backward due to the pulling force exerted on the string 7. The web 1 is thus invaginated during the removal step.

In FIG. 27, the flaps 6, 6' gradually unstick from the vaginal wall 18 during the removal of the central zone 13, thereby limiting the irritations due to the removal forces. In fact, in the known tampon systems, the attachment zone of the string 7 being situated near the outlet orifice of the vaginal cavity 17, it results that the removal forces applied on the tampon are shearing forces, sources of irritation of and sometimes damage to the vaginal wall 18.

It is preferable to provide an attachment of the string 7 on only part of the width of the web 1, so that the backward movement of the central zone 13 causes a gradual unsticking of the longitudinal edges 3 toward the back and center of the web 1. Furthermore, this removal movement will make it possible to capture the discharges and secretions inside the invaginated web 1, consequently making the removal act more clean and comfortable for the user, since stains will not come into direct contact with the outside of the vaginal cavity 17.

FIGS. 28 to 30 are longitudinal diagrammatic cross-sectional views illustrating the successive steps of freeing an agent 16, of the dry vaginal suppository type for example, equipping a specific applicator member. More specifically, this applicator member has a distal end 11 made in the form of a substantially conical segment:

having a passage section whereof the diameter is smaller than that of the body 8. As a result, this conical segment allows better intromission without hurting the vaginal wall 18, being designed so as to have a radial elasticity. It is thus possible to slide or introduce an agent 16 easily into the pouch 30 owing to the radial flexibility of the conical segment.

This conical segment facilitates the manipulation of the device by the user as it makes it possible to keep the agent 16 in the pouch 30, even in the case of a wrong movement by the user.

A tubular release member 40 having a conical pushing end 41 is slid inside the body 8. During the sliding of the release member 40 into the body 8, the pushing end 41 comes into contact with the central zone 13 and the agent 16, driving the latter until it is freed outside the pouch 30.

As shown in detail in FIG. 31, the body 8 advantageously has a reduced thickness of material at the conical segment of the distal end 11 relative to the rest of said body 8, and the distal end 11 has a bead 50.

In this way, the conical segment has an increased deformation capacity allowing it to conform naturally to the geometry of the vaginal cavity during the intromission of the device, and the presence of the bead 50 at the end makes it possible to avoid excessive radial crushing of the conical segment during the intromission. In so doing, it is thus possible to still further reduce any risk of untimely injury of the vaginal wall by friction.

Furthermore, the substantially circular geometry in cross-section of the bead 50 greatly facilitates the unrolling of the web 1 during the intromission. The forces to be applied on the web to cause it to unroll can therefore be greatly reduced.

Such a type of body 8 is particularly appropriate to deliver an agent 16.

Alternatively, and as shown in FIG. 32, a body 8 of another device according to the invention can be made so as to have a globally cylindrical general shape.

As previously described, the body 8 advantageously has a reduced material thickness at the distal end 11 relative to the rest of said body 8, and the distal end 11 has a bead 50.

In general, and so as to facilitate the placement of the web 1 in the vaginal wall, it may be advantageous to use a web 1 having, on the one hand, a "velvet"-type surface intended to come into contact with the vagina during intromission and favoring adhesion between the web 1 and the vaginal wall, and on the other hand, another smooth surface with exemplary sliding so as to decrease the resistance or friction with the distal end 11 of the body 8.

Although the invention has been described relative to specific embodiments, it is of course in no way limited thereto and comprises all technical equivalents of the described means as well as combinations thereof if they are within the scope of the invention.

The invention claimed is:

1. A device comprising an applicator member and a flexible retention web (1) intended to be introduced into a vaginal cavity (17), said web being equipped with a removal means (7) and being made from an atraumatic material whereof the dimensions are adapted so as to be able to retain and/or slow down bodily discharges of small quantity, characterized in that:
    the applicator member comprises a body (8) that is at least partially hollow defining an internal storage volume (9), said body having a proximal end (10) on the one hand, and on the other hand, a distal end (11) intended to be inserted into the vaginal cavity of a user, said distal end having an open section emerging in the internal storage volume,
    the web comprises a central zone (13) housed in the internal storage volume, and at least one peripheral zone (14) protruding from the body and folded to cover at least the distal end of the body.

2. The device according to claim 1, characterized in that the applicator member is made in the form of a tubular body (8).

3. The device according to claim 2, characterized in that the distal end is made in the form of a substantially conical segment so as to have a reduced passage section relative to the diameter of the body (8), and in that the segment is designed so as to have a radial elasticity.

4. The device according to claim 1, characterized in that the web (1) is made from a material chosen from amongst the group formed by a nonwoven textile, polyvinyl acetate, cotton, an organic material, a plant material, or a biodegradable material.

5. The device according to claim 1, characterized in that the web (1) is designed such that it can convey at least one therapeutic or non-therapeutic agent.

6. The device according to claim 1, characterized in that the web (1) is made in a substantially rectangular, square, oval or circular shape.

7. The device according to claim 1, characterized in that the web (1) comprises at least two flaps (6, 6') folded onto each other.

8. The device according to claim 7, characterized in that each of the two flaps (6, 6') is extended by the removal means (7).

9. The device according to claim 1, characterized in that the removal means (7) is attached to the central zone (13) of the web, and in that the body (8) of the applicator member is hollow.

10. The device according to claim 9, characterized in that the removal means (7) is disposed along the transverse axis (5).

11. The device according to claim 1, characterized in that the web (1) incorporates at least one fluid barrier made using a hydrophobic material.

12. The device according to claim 1, wherein the web has little or no absorbency, and wherein the web has a thickness adapted to allow the formation of a pouch in the internal volume of the applicator member.

13. A method for manufacturing a device comprising an applicator member and a flexible retention web (1) intended to be introduced into a vaginal cavity (17), said web being equipped with a removal means (7) and being made from an atraumatic material whereof the dimensions are adapted so as to be able to retain and/or slow down bodily discharges of small quantity, wherein the applicator member comprises a body (8) that is at least partially hollow defining an internal storage volume (9), said body having a proximal end (10) on the one hand, and on the other hand, a distal end (11) intended to be inserted into the vaginal cavity of a user, said distal end having an open section emerging in the internal storage volume, and the web comprises a central zone (13) housed in the internal storage volume, and at least one peripheral zone (14) protruding from the body so as to cover at least the distal end of the body, the method characterized in that it comprises the following steps:
    cutting a web (1) in a band (2),
    depositing and fastening, on the web, at least one string (7), forming a removal means, the length of the string being chosen to be greater than the largest length of the web so that the string protrudes on either side of the web,
    depositing the applicator member (8) along part of the web, so that, on the one hand, the proximal end (10) protrudes from the web, and on the other hand, the distal end (11) rests on the web,
    folding the web around a transverse axis (5), and folding the web on the applicator member,
    inserting the central zone (13) of the web into the internal volume (9) of the applicator member using an insertion member (12).

14. The manufacturing method according to claim 13, characterized in that a single string (7) is deposited and secured substantially along the median longitudinal axis of the web (1).

15. The manufacturing method according to claim 13, characterized in that a string (7) is deposited and secured along each of the two longitudinal edges (3) of the web (1).

16. The manufacturing method according to claim 13, characterized in that the applicator member (8) is deposited so that its distal end (11) is situated substantially at mid-length of the web (1).

17. The manufacturing method according to claim 13, characterized in that a notch (4) is cut into each of the two longitudinal edges (3) of the web (1) at the transverse axis (5).

18. The manufacturing method according to claim 13, characterized in that at least one therapeutic or non-therapeutic agent is injected on the central zone (13) of the web (1) through at least one conduit (15) and an injection opening (15') of the insertion member (12).

19. The manufacturing method according to claim 13, characterized in that, before insertion of the central zone (13) of the web (1) into the internal volume (9), a therapeutic or non-therapeutic agent (16) is positioned between the central zone of the web and the insertion member (12).

20. The manufacturing method according to claim 19, characterized in that the length of the web (1) is chosen so that, after complete insertion of the applicator member (8)

into the vaginal cavity (17), part of the central zone (13) of the web as well as the agent (16) remain in the internal volume (9).

* * * * *